US010792690B2

(12) United States Patent
Friend et al.

(10) Patent No.: US 10,792,690 B2
(45) Date of Patent: Oct. 6, 2020

(54) ATOMISATION APPARATUS USING SURFACE ACOUSTIC WAVE GENERATION

(71) Applicant: RMIT UNIVERSITY, Melbourne (AU)

(72) Inventors: James Friend, Victoria (AU); Leslie Yeo, Victoria (AU); Aisha Qi, Victoria (AU)

(73) Assignee: RMIT UNIVERSITY, Melbourne (AU)

( * ) Notice: Subject to any disclaimer, the term of this patent is extended or adjusted under 35 U.S.C. 154(b) by 793 days.

(21) Appl. No.: 14/769,490

(22) PCT Filed: Feb. 28, 2014

(86) PCT No.: PCT/IB2014/059321
§ 371 (c)(1),
(2) Date: Aug. 21, 2015

(87) PCT Pub. No.: WO2014/132228
PCT Pub. Date: Sep. 4, 2014

(65) Prior Publication Data

US 2016/0001316 A1 Jan. 7, 2016

(30) Foreign Application Priority Data

Mar. 1, 2013 (AU) ................................ 2013900690

(51) Int. Cl.
*B05B 17/00* (2006.01)
*A61M 11/00* (2006.01)
(Continued)

(52) U.S. Cl.
CPC ............ *B05B 17/0646* (2013.01); *A61L 9/14* (2013.01); *A61M 11/005* (2013.01);
(Continued)

(58) Field of Classification Search
CPC ............ B05B 17/0646; B05B 17/0676; B05B 17/0684; B05B 17/0607; B05B 17/0615;
(Continued)

(56) References Cited

U.S. PATENT DOCUMENTS 2,898,596 A * 8/1959 Keen ..................... A63B 71/10
2/421
4,753,579 A * 6/1988 Murphy .................. F04D 33/00
239/102.2
(Continued)

FOREIGN PATENT DOCUMENTS

EP 0897755 A2 2/1999
JP 2008-073570 A 4/2008
(Continued)

OTHER PUBLICATIONS

E.M. Garber et al.; Design of High Selectivity DART SPUDT Filters on Quartz and Lithium Tantalate; 1994 Ultrasonics Symposium.*

(Continued)

*Primary Examiner* — Victoria Murphy
(74) *Attorney, Agent, or Firm* — BakerHostetler

(57) ABSTRACT

An apparatus for atomising liquid, including a piezoelectric substrate (1) having a working surface (3), and a peripheral edge (7) extending along a side of the working surface, an interdigital transducer (2) located on the working surface for generating surface acoustic waves (SAW) in the working surface, and a liquid delivery arrangement including a porous member (8) for supplying the liquid to be atomised, wherein the porous member is in contact with the peripheral edge of the piezoelectric substrate.

12 Claims, 3 Drawing Sheets

(51) Int. Cl.
  *A61M 15/00* (2006.01)
  *B05B 17/06* (2006.01)
  *B06B 1/06* (2006.01)
  *A61L 9/14* (2006.01)

(52) U.S. Cl.
  CPC ..... *A61M 15/0085* (2013.01); *B05B 17/0607* (2013.01); *B05B 17/0615* (2013.01); *B05B 17/0676* (2013.01); *B05B 17/0684* (2013.01); *B06B 1/0644* (2013.01); *A61L 2209/132* (2013.01); *A61M 2202/09* (2013.01); *A61M 2205/0294* (2013.01); *A61M 2210/065* (2013.01)

(58) Field of Classification Search
  CPC ... A61L 9/14; A61L 2209/132; B06B 1/0644; A61M 11/005; A61M 15/0085
  See application file for complete search history.

(56) References Cited

U.S. PATENT DOCUMENTS

| | | | | |
|---|---|---|---|---|
| 4,793,339 | A * | 12/1988 | Matsumoto | B05B 17/0623 128/200.16 |
| 5,716,002 | A * | 2/1998 | Haack | B05B 17/0607 239/102.1 |
| 5,952,765 | A | 9/1999 | Garber et al. | |
| 6,137,207 | A * | 10/2000 | Inoue | H03H 9/0259 310/313 A |
| 6,368,482 | B1 * | 4/2002 | Oeftering | C25D 5/02 204/222 |
| 6,601,581 | B1 * | 8/2003 | Babaev | A61M 15/0085 128/200.16 |
| 7,075,390 | B1 * | 7/2006 | Bungo | H03H 9/0259 310/313 A |
| 8,991,722 | B2 * | 3/2015 | Friend | A61M 15/025 239/102.2 |
| 2001/0042794 | A1 * | 11/2001 | Tomkins | A61L 9/14 239/102.2 |
| 2005/0126480 | A1 * | 6/2005 | Yamagata | B01J 19/0046 118/621 |
| 2007/0232962 | A1 * | 10/2007 | Zumeris | A61H 23/0236 601/2 |
| 2007/0284090 | A1 * | 12/2007 | Wu | F28D 15/0266 165/104.26 |
| 2008/0053787 | A1 * | 3/2008 | Bagajewicz | B01D 61/00 196/111 |
| 2008/0054091 | A1 * | 3/2008 | Babaev | B01F 3/08 239/102.2 |
| 2008/0230052 | A1 * | 9/2008 | Montaser | A61M 15/0085 128/200.16 |
| 2011/0068193 | A1 * | 3/2011 | Machi | B05B 17/0607 239/102.1 |
| 2011/0148253 | A1 * | 6/2011 | Friend | H02N 2/003 310/323.02 |
| 2011/0192914 | A1 * | 8/2011 | Ishigami | F24F 6/12 239/102.2 |
| 2012/0187209 | A1 * | 7/2012 | Friend | A61P 11/06 239/4 |
| 2013/0079733 | A1 * | 3/2013 | Burt | B05B 17/0615 604/290 |
| 2013/0161407 | A1 * | 6/2013 | Hielscher | B05B 17/0607 239/4 |
| 2013/0277446 | A1 * | 10/2013 | Selby | B05B 17/0669 239/4 |
| 2014/0083174 | A1 * | 3/2014 | Reboud | B05B 17/0653 73/61.59 |
| 2014/0319237 | A1 * | 10/2014 | Brothier | B22F 1/0096 239/4 |

FOREIGN PATENT DOCUMENTS

| | | | |
|---|---|---|---|
| JP | 2008-104966 A | 5/2008 | |
| JP | 2010-269278 A | 12/2010 | |
| JP | 2011-121050 A | 6/2011 | |
| JP | 2012-143726 A | 8/2012 | |
| WO | WO 2010/129904 A1 | 11/2010 | |
| WO | WO 2012/096378 A1 | 7/2012 | |
| WO | WO 2012096378 A1 * | 7/2012 | ......... B05B 17/0607 |

OTHER PUBLICATIONS

Qi et al. Miniature inhalation therapy platform using surface acoustic wave microfluidic atomization; Lab on a Chip 2009; The Royal Society of Chemistry.*

Hartman et al., "Overview of design challenges for single phase unidirectional SAW filters", Invited Paper, IEEE Ultrasonics Symposium, Oct. 1989, 79-82.

* cited by examiner

ATOMISATION APPARATUS USING SURFACE ACOUSTIC WAVE GENERATION

CROSS-REFERENCE TO RELATED APPLICATIONS

This application is the National Stage of International Application No. PCT/IB2014/059321, filed Feb. 28, 2014, which claims the benefit of Australian Application No. 2013900690, filed Mar. 1, 2013, the disclosures of which are incorporated herein by reference in their entireties.

FIELD OF THE INVENTION

The present invention is generally directed to apparatus for atomising liquids, and in particular to apparatus using surface acoustic wave (SAW) generation to atomise liquid. While the present invention will be described with reference to its use in medical applications, it is to be appreciated that the invention is not restricted to this application, and that other applications are also envisaged.

BACKGROUND OF THE INVENTION

Inhalation therapy is used to deliver pharmaceutical or other substances into the lungs of patients. In order for inhalation therapy to be effective, the liquid containing the substance to be delivered needs to be atomised to produce liquid droplets of a size that will allow the droplets to be readily inhaled and deposited within the patient's lungs. The droplets need to be less than 5 μm for deep lung deposition, and be of a larger size if deposition is required higher in the airways.

Atomisation apparatus using surface acoustic wave (SAW) propagation to atomise liquid have been considered for use for inhalation therapy. This is because they can potentially provide designs that are portable and allow for greater control of the atomisation rate and droplet size. These apparatus typically include a piezoelectric substrate having an upper working surface, and an interdigital transducer located on the upper working surface. Application of RF power to the interdigital transducer results in the generation of surface acoustic waves in the upper working surface. Liquid to be atomised is supplied to the upper working surface. While the amplitude of the surface vibration of the SAW is only in the order of 1 nm, the SAW is typically driven with a frequency over 10 MHz. This results in an acceleration as high as $10^7$ m/s$^2$, leading to strong liquid actuation when the SAW meets the liquid supported on the working surface. The acceleration is sufficient to overcome the capillary-viscous stress within the liquid and to break up the capillary wave generated in the liquid into micron sized aerosols. This is what is known as SAW atomisation.

Japanese Publication No. 2008-104966 (Seiko Epson Corp) describes a SAW atomisation apparatus which uses a porous member in contact with the upper working surface of a SAW actuator to supply liquid to that upper working surface for atomisation. The porous member acts as a wick to draw liquid from a reservoir to the upper working surface.

International publication no. WO 2010/129904 (Monash University) describes a SAW atomisation apparatus which is particularly applicable for use in inhalation therapy. An EWC-SPUDT type interdigital transducer is used to focus the SAW generated in the upper working surface of the piezoelectric substrate to a focus point leading to increased atomisation efficiency. The liquid to be atomised is supplied directly to the working surface of the SAW actuator through a thin paper wick in contact with the working surface. The liquid supplied to the working surface forms a liquid meniscus at the edge of the paper wick from which atomisation can take place.

The Applicants has found that in atomisation apparatus using SAW generation, supplying fluid directly to the working surface can lead to an overall loss of energy limiting the operational energy efficiency of the apparatus. This is because liquid supplied to the working surface of the SAW actuator participates in the vibration of the working surface prior to breaking up into atomised liquid droplets. The liquid, prior to atomisation, therefore absorbs some of the energy associated with the generated SAW limiting the operational energy efficiency of the apparatus. Furthermore, results have shown that part of the SAW energy is absorbed by the first 1 to 3 mm of the wick at the interface of the wick with the liquid meniscus.

Because of the limitation on the operational energy efficiency of such atomisation apparatus, relatively high power, typically around 3 to 6 watts, therefore needs to be applied to the interdigital transducer of the SAW actuator to operate correctly. This can lead to high localised heating at the transducer which can contribute to premature failure of the apparatus.

It would be advantageous to provide an atomisation apparatus with improved operational energy efficiency compared with prior art designs.

It is also preferably advantageous to provide an atomisation apparatus having improved reliability compared with prior art designs.

With this in mind, the present invention provides an apparatus for atomising liquid, including a piezoelectric substrate having a working surface, and a peripheral edge extending along a side of the working surface, an interdigital transducer located on the working surface for generating surface acoustic waves (SAW) in the working surface, and a liquid delivery arrangement including a porous member for supplying the liquid to be atomised, wherein the porous member is in contact with the peripheral edge of the piezoelectric substrate.

As previously noted, the applicants have found that liquid supplied directly to the working surface using a wick in contact with the working surface will also participate in the vibration of that working surface prior to atomisation resulting in a loss of energy, and thereby limiting the overall operational energy efficiency of the atomisation apparatus. This energy loss is avoided according to the present invention by not supplying the liquid to be atomised directly to the working surface using a wick in contact with that surface. The piezoelectric substrate typically has a planar configuration with an upper working surface and peripheral edge surfaces extending along the periphery of the piezoelectric surface. The peripheral edge surface therefore extends at an angle, typically around 90 degrees, relatively to the plane of the working surface. The peripheral edge of the piezoelectric substrate is located where the peripheral edge surface meets the upper working surface of the piezoelectric substrate. The interaction of the SAW at the peripheral edge with the liquid being supplied by the porous member leads to formation of a thin liquid layer having a relatively large meniscus area from which atomisation of the liquid can occur. The SAW excitation at the peripheral edge of the piezoelectric substrate results in liquid being drawn from the porous member onto the working surface. Limiting the contact area of the porous member to the peripheral edge of the piezoelectric substrate limits the SAW energy being absorbed by the porous member helping to minimise energy loss from the apparatus.

The Applicants have studied the fluid flow mechanisms that help to drive liquid motions within SAW atomisation apparatus. It is the Applicant's understanding that the dominant mechanism driving liquid motion within a thin boundary layer adjacent to the working surface is "Schlichting" streaming (or boundary layer streaming). This mechanism drives liquid motion within the thin boundary layer through viscous shear which results in a net liquid motion towards the source of the SAW irradiation. This results in liquid being drawn from the porous member to form a liquid layer over the working surface adjacent the peripheral edge, the liquid layer having a liquid meniscus from which atomisation can take place.

It is preferable for the thickness of the liquid layer formed over the working surface adjacent the peripheral edge to be close to, or the same as the thickness of the boundary layer produced immediately above the working surface where the liquid directly interacts with the SAW vibration. This therefore allows the Schlichting streaming mechanism to dominate the the driving of the liquid within the liquid layer. The advantage provided by this is that it limits or prevents the appearance of what is known as "Eckart" streaming within the meniscus. Eckart streaming acts to drive flow in the bulk of the liquid in the direction of the SAW generation, and therefore in opposition to the Schlichting streaming. This can result in the production of aerosols of a large and therefore unsatisfactory size, for example greater than 100 μm in diameter.

The thickness of the boundary layer will be generally the same as the wavelength of the SAW propagating through the liquid. This wavelength may be determined using the following equation:

$$\lambda_f = c_f/f = 50\ \mu\text{m}$$

where $\lambda_f$ is the wavelength of the SAW generated in the working surface $c_f$ is the travelling velocity of the SAW in water which is 1482 m/s; and f is the frequency of operation which is for example 30 MHz.

Therefore the boundary layer may have a thickness of about 50 μm, and the maximum thickness of the liquid layer is then preferably equal to or less than 50 μm. This is difficult to produce using a wick in direct contact with the working surface as in prior art SAW atomisation apparatus as the wick needs to be limited in thickness to 50 μm or less to enable a liquid layer of that thickness to be produced. This may be achieved, according to a preferred aspect of the invention, by positioning the porous member relative to the peripheral edge such that an upper surface of the porous member is spaced from the working surface at a distance generally corresponding to the desired thickness of the liquid layer. The liquid is then drawn from the portion of the porous member extending above the peripheral edge to thereby form a liquid layer on the working surface having the desired thickness. It is therefore not necessary to limit the thickness of the porous member as would be required where a porous wick was in contact with the working surface.

The porous member may preferably be formed from porous cellulose material which provides for controlled delivery of liquid. The porous member may for example be made from a biodegradable hydroxypropyl cellulose (HPC). The porous member may be shaped to thereby allow one end of the porous member may be in contact with at least one point on said peripheral edge of the piezoelectric substrate. Alternatively, the porous member may contact a length of the peripheral edge. The SAW may be focused at the part of the peripheral edge contacted by the porous member. The shape and pore size within the porous member can act to control the flow rate of liquid to the peripheral edge. The opposing end of the porous member may be supported within a container containing the liquid to be atomised. The end of the porous member within the liquid container may be located within a support element formed from absorbent material. This support element, in addition to supporting the porous member, also assists in transferring liquid from the container to the porous member.

Interdigital transducers (IDT) typically include a positive electrode and a negative electrode. Electrode fingers respectively extend from the positive and negative electrodes, the electrode fingers being located in an interlaced relationship on the working surface of the piezoelectric substrate. The IDT of the apparatus according to the present invention may preferably be a single phase, unidirectional transducer (SPUDT). The use of SPUDTs provides advantages over traditional IDTs. In a SAW actuator using a traditional IDT, the SAW propagates in both forward and reverse directions in the working surface. This is because the SAW is reflected back to the IDT from the edge of the SAW actuator. These reflections interfere with the forward moving SAW leading to a considerable loss in SAW energy. By comparison, the SAW generated from a SPUDT propagates in a single direction only. This is achieved by superimposing internally tuned reflector fingers between each pair of electrode fingers. These reflector fingers may be formed as electrode fingers extending from at least one of the electrodes. The placement of these reflector fingers enhances the SAW in the forward direction, and suppresses the SAW in the reverse direction. Therefore, less SAW energy is lost using a SPUDT, and the risk of interfering reflections is reduced.

Such SPUDTs can also be designed to focus the energy of the generated SAW to a predetermined area on the working surface by curving the fingers, preferably along an elliptical curve. The SPUDT may therefore focus the SAW to an area immediately adjacent a said peripheral edge surface of the piezoelectric substrate. The focus area may preferably be located immediately adjacent where the porous member is in contact with the peripheral edge surface. Alternatively, the SAW may be focused along a line aligned with the peripheral edge surface contacting the porous member.

The SPUDT may preferably be of a DART-SPUDT type. A DART-SPUDT has several advantages over other known SPUDTs, including the EWC-SPUDT electrode described in the previously mentioned International Publication No. WO 2010/299904. In SPUDTs, the width of each electrode finger, including the reflector fingers, is a function of the wavelength (λ) generated by the electrode. In a DART-SPUDT, the reflector fingers is ⅜ λ in width, while the reflector fingers of a EWC-SPUDT is ¼ λ in width. Also, the reflector fingers of a Hanma-SPUDT are $\frac{3}{16}$ λ in width. The reflector fingers of an EWC-SPUDT and a Hanma-SPUDT are therefore more narrow than the reflector fingers of a DART-SPUDT. The advantage of having an electrode with relatively wider reflector finger width is that this reduces the effect of electrode resistance and Joule heating thereby reducing the power required to be applied to the electrodes, and reducing localised heating of the transducer. Furthermore, the cost of producing the interdigital transducers on the piezoelectric substrate using manufacturing processes such as photolithography is significantly reduced when compared with interdigital transducers having narrower electrode fingers. In addition, the number of SAW actuators that need to be rejected due to defective interdigital transducers is significantly reduced.

It has also been identified by the Applicant that the thickness of the metal layer forming the IDT performs an important role in reducing power loss. It has been found that IDTs having a thickness of at least 1% the SAW wavelength, and preferably between 1 to 5% of the SAW wavelength are more efficient in delivering energy to the piezoelectric substrate. Normal IDTs have a thickness significantly less than this. Therefore, using the above mentioned equation, the IDT thickness may be between 1.32 and 6.6 µm, where the travelling velocity of the SAW is 3965 m/s in the piezoelectric substrate and the frequency of operation of the SAW actuator is 30 MHz. There are a number of advantages provided by the additional thickness of the IDT. Firstly, it reduces the resistance, and consequently, the impedance of the IDT thereby improving the efficiency of the SAW actuator. This is particularly critical where the atomisation apparatus is battery powered. Another advantage is that the temperature of the SAW actuator is significantly reduced, typically from around 80° C. to about 50° C. This is particularly important where biological and chemical carrying liquids, as such liquids are not able to handle high temperatures. For example, stem cells are unable to handle high temperatures, but are able to be delivered using the atomisation apparatus according to the present invention. The reduced operational temperature also improves the reliability of operation of the atomisation apparatus. This is because localised heating at the IDT is a direct contributor to premature failure of the device. In addition, the greater thickness of the IDT is useful in the case of SPUDT type transducers as it is useful in assisting in blocking the SAW reflections travelling in the reverse direction.

In prior art atomisation apparatus using SAW actuation, the power required to achieve atomisation is around 3 to 6 Watt, with the input voltage being as high as 60 V peak to peak (~20 $V_{RMS}$). By comparison, the present invention can preferably achieve atomisation with a greatly reduced power of 0.5-3 Watts, with the input voltage also at a much lower and safer range at only around 30 Volts peak-to-peak (~10 $V_{RMS}$). This is in large part because of the thickness of the IDT used that reduces the resistance, and consequently the impedance of the SAW actuator improving the efficiency of the apparatus as previously explained. The lower power and voltage requirements are important for consumer devices to assist in compliance with current safety regulations. It has been found that atomisation rate of over 200 µl/min can be achieved with the above mention power and voltage in an apparatus according to the present invention. By comparison, prior art apparatus need as much as 20 $V_{RMS}$ to achieve the same rate.

It should be noted that terms such as "upper" and "side" used to describe the relative positions of features of the present invention and therefore relate to one specific orientation of the atomisation apparatus. As the atomisation apparatus can also be used in alternative orientations, the use of the above-noted terms are not intended to limit the scope of the invention to being in that specific orientation.

The lower operational temperature of the atomisation apparatus according to the present invention, and therefore, the lower temperature of the aerosols/droplets produced allows for the delivery of biological substances such as the stem cells previously referred to which would otherwise be damaged if exposed to the higher operational temperatures of less efficient prior art apparatus. The atomisation apparatus may however also be used in other applications such as the atomisation of liquids containing fragrant substances, and chemicals and pharmaceuticals such as antibiotics for delivery into a single or multiple rooms of a building. Other potential uses for the apparatus include the delivery of fragrant substances such as perfumes and scents for both personal and room applications. It is also possible for the apparatus to be used to deliver cosmetic substances, prays for the mouth and throat of a person, sprays with cleaning, sterilizing, and anti-allergy substances, or agricultural chemicals such as herbicides, fungicides, insecticides and fertilizers. Other applications of the atomisation apparatus according to the present invention are also envisaged.

BRIEF DESCRIPTION OF THE DRAWINGS

It will be convenient to further describe the invention with reference to the accompanying drawings which illustrate a preferred embodiment of the present invention. Other embodiments are possible and, consequently, the particularity of the accompanying drawings is not to be understood as superseding the generality of the preceding description of the invention.

In the drawings.

DETAILED DESCRIPTION OF THE INVENTION

Figure 1:
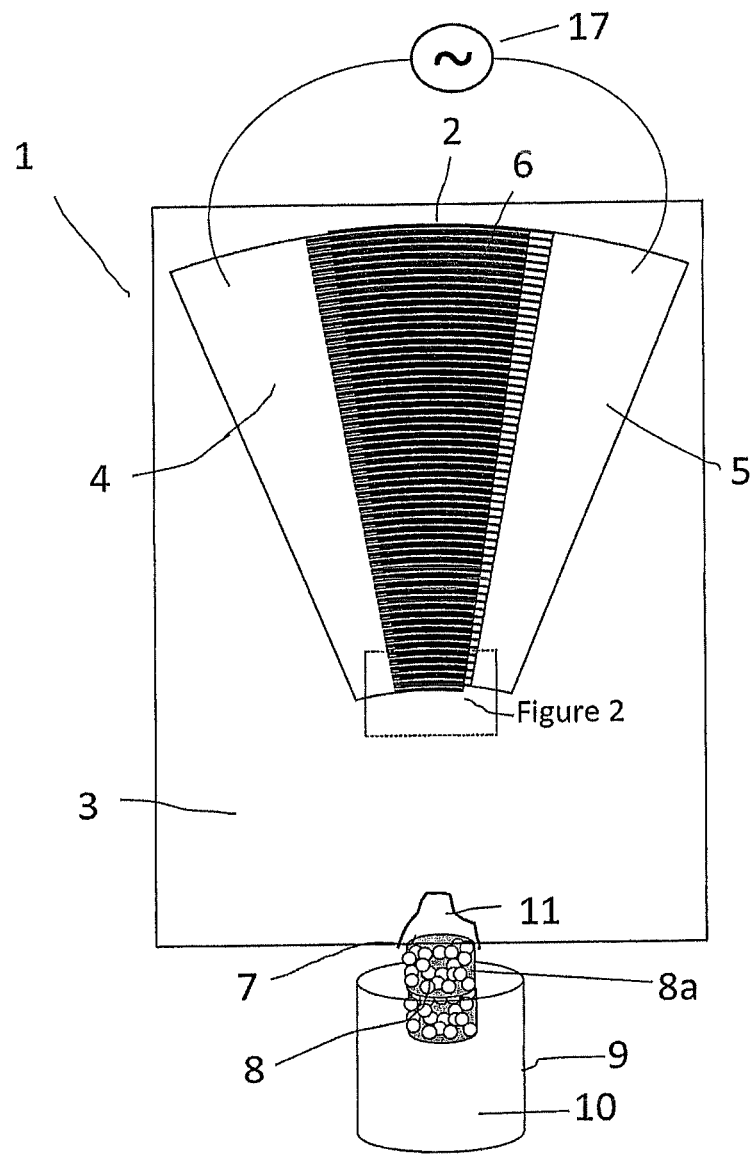
FIG. 1 is a schematic top view of an atomisation apparatus according to the present invention.

Referring initially to FIG. 1, the SAW atomisation apparatus according to the present invention includes a piezoelectric substrate 1 which is typically formed from lithium niobate ($LiNbO_3$). Unlike more commonly used piezoelectric material such as lead zironate titanate (PZT), $LiNbO_3$ is lead free and therefore safe to use in medical applications. The piezoelectric substrate 1 has an upper working surface 3 through which an SAW can be generated. A peripheral edge 7 extends along the outer periphery of the piezoelectric substrate 1.

An interdigital transducer, preferably of a DART-SPUDT type, is located on the working surface 3. The interdigital transducer 2 includes a positive electrode 5 and a negative electrode 4, with electrode fingers 6 respectively extending from the positive and negative electrodes. The electrode fingers 6 of each electrode 4,5 are located in an interlaced relationship. Application of an electrical signal to the transducer element 2 results in the generation of an SAW through the working surface 3 of the piezoelectric substrate 1.

Figure 3:
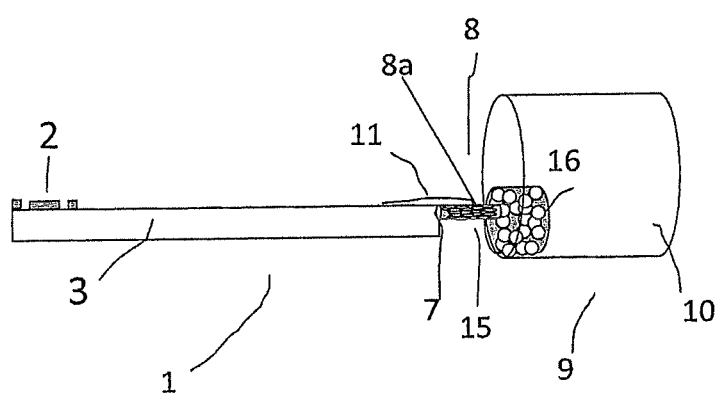
FIG. 3 is a detailed side view of the atomisation apparatus of FIG. 1 showing the liquid delivery arrangement of the apparatus of FIG. 1.
Figure 4:
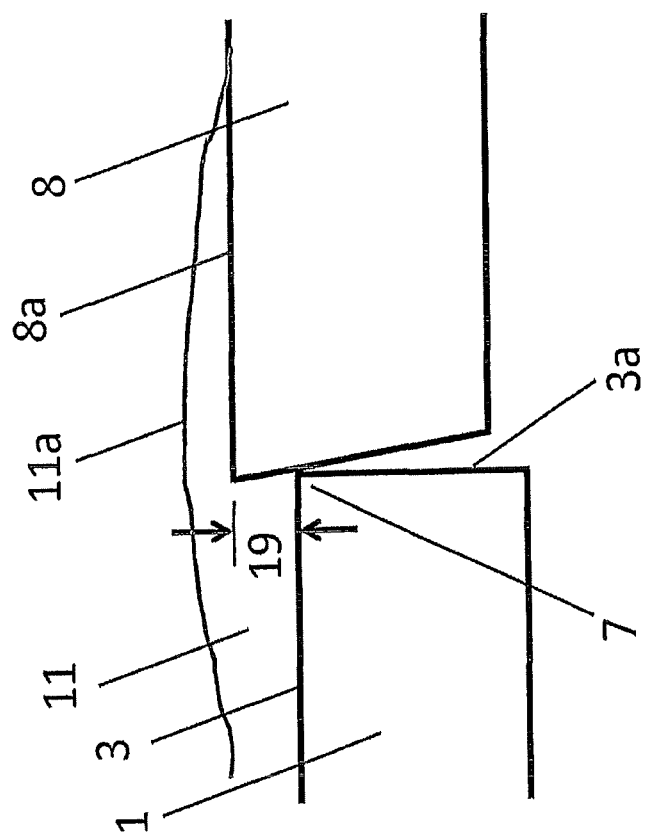
FIG. 4 is a detailed schematic view of the contact area of the peripheral edge of the piezoelectric substrate and the porous member of the atomisation apparatus of FIG. 1.

The liquid 10 to be atomised is accommodated within a liquid container 9. A porous member 8 extends from the liquid container 9, with one end of the porous member being in contact with the peripheral edge 7 of the piezoelectric substrate 1. The other end of the porous member 8 is supported by an absorbent support element 16 located within the liquid container 9. The support element 16 (as shown in FIG. 3), as well as supporting the porous member 8, also facilitates the transfer of the liquid 10 from the container 9 through into the porous member 8. The porous member may for example be made from a polymer cellulose such as biodegradable hydroxypropyl cellulose (HPC). The use of other hydrophilic materials for the porous member 8 is also envisaged.

Figure 2:
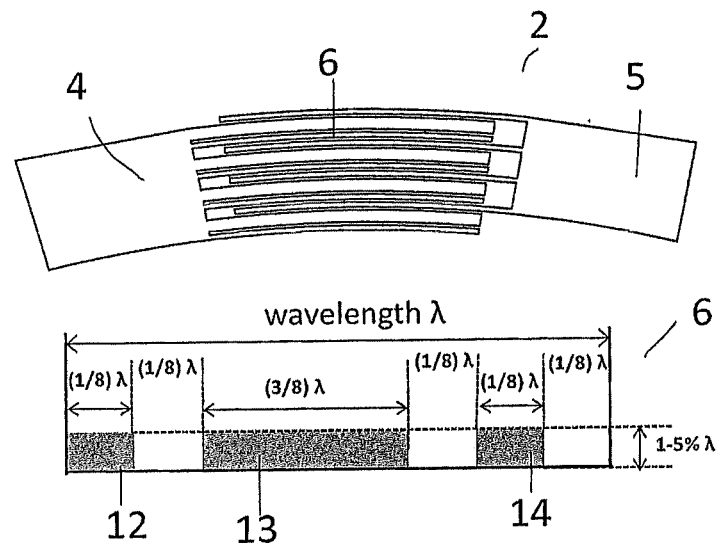
FIG. 2 respectively show a plan view and detailed cross-sectional view of an interdigital electrode of the atomisation apparatus of FIG. 1.

Referring now to FIG. 2 which provides a detailed view of the interdigital transducer 2, the electrode fingers 6 may have a elliptical or circular curved configuration. This arrangement allows the energy of the generated SAW to be directed to a predetermined area on the peripheral edge 7. In the SAW atomisation apparatus according to the present invention, the SAW can be directed to an area immediately adjacent to where the porous member 8 contacts the peripheral edge 7. It is also envisaged that the electrode fingers 6 be straight, in which case the generated SAW may be directed along a line extending parallel to the peripheral edge 7 contacting the porous member 8.

Extending from the negative electrode 4 are reflector fingers 13 that are wider than the other electrode fingers 12, 14. The purpose of the reflector fingers 13 is to prevent the reflections of the SAW in a reverse direction to the SAW propagating from the DART-SPUDT transducer 2, thereby minimising the loss of energy from the generated SAW. A DART-SPUDT transducer 2 differs from other SPUDT transducers, for example an EWC-SPUDT or Hanma-SPUDT type, in that the reflector fingers 13 have a width of $3/8 \lambda$ as shown in FIG. 2, $\lambda$ being the wavelength of the generated SAW. By comparison, an EWC-SPUDT has reflector fingers with a width of $1/4 \lambda$, and a Hanma-SPUDT has reflector fingers with a width of $3/16 \lambda$. DART-SPUDT transducers therefore have the widest reflector fingers of these SPUDT types. The use of larger SPUDTs has the benefit of reducing the effects of electrode resistance and Joule heating. Another advantage of having larger sized interdigital transducers is that it is easier to deposit the transducer 2 on the piezoelectric substrate 1 using photolithographic techniques. The transducer 2 can therefore be deposited with greater accuracy leading to a lower defect rate for these transducers.

FIG. 2 shows in more detail the configuration of a DART-SPUDT transducer. The positive electrode 5 has an electrode finger 14 with a width of $1/8 \lambda$, the positive electrode finger 14 being located and aligned with a negative electrode finger 12, and a reflector finger 13 extending from the negative electrode 4. The positive and negative electrode fingers 12, 14 and the reflector finger 13 are respectively spaced apart a distance of $1/8 \lambda$.

As also shown in FIG. 2, the thickness of the interdigital transducer 2 may be greater than 1% $\lambda$, $\lambda$ being the SAW wavelength. It is preferred that the thickness of the interdigital transducer 2 be between 1 to 5% $\lambda$. The transducer 2 therefore has a thickness that is greater than the thickness of traditional interdigital transducers. The greater thickness of the electrode fingers 6 results in lower relative impedance through the transducer 2 thereby improving the efficiency of the SAW atomisation apparatus. The improved efficiency means that a relatively lower amount of power need be applied to the transducer 2 to operate correctly. This furthermore reduces the local temperature of the aerosols that leave the apparatus to around 50° C.

The SAW generated within the working surface 3 moves in a general direction towards the peripheral edge 7 in contact with the porous member 8. When the SAW reaches the peripheral edge of the working surface 3, a physical phenomenon known as Schlichting streaming acts to draw liquid 10 from the porous member 8. The result of this Schlichting streaming phenomenon is that the liquid will try to move towards the source of the SAW. This results in an accumulation of liquid, in a thin liquid layer 11 adjacent the peripheral edge 7. This thin liquid layer 11 can extend across the working surface 3 from the peripheral edge 7. The thin liquid layer 11 may also extend over onto the upper surface 8*a* of the porous member 8 as shown in FIG. 3. This liquid volume forms a liquid meniscus 11*a* from which is generated the atomised liquid droplets.

FIG. 4 shows in more detail the configuration of the atomisation apparatus where the porous member 8 contacts the peripheral edge 7 of the piezoelectric substrate 1. The peripheral edge 7 is located where the working surface 3 meets a side surface 3*a* of the piezoelectric substrate 1. FIG. 4, only shows the porous member 8 contacting the piezoelectric substrate 1 at the peripheral edge 7. It is however also possible for the porous member 8 to contact the side surface 3*a* of the piezoelectric substrate 1. The porous member 8 is located relative to the peripheral edge 7 such that the upper surface 8*a* of the porous member 8 is spaced a fixed distance 19 from the working surface 3. This distance 19 is preferably equal to or less than the boundary layer thickness which is generally equal to the wavelength of the SAW propagating though the working surface 3. This helps to ensure that the maximum thickness of the liquid layer 11 extending from the peripheral edge 7 is similar to the boundary layer thickness. This will help to ensure that Schlichting streaming dominates the liquid motion so that the liquid can be drawn from the porous member 8 to form the liquid layer 11, and that the liquid can subsequently be atomised to an optimal size from the meniscus 11*a* of that liquid layer 11.

As only a relatively small amount of liquid is drawn at any one time over the working surface, there is little involvement of that liquid volume with the SAW vibration generated in the working surface 3 leading to a reduced loss of energy from the atomisation apparatus when compared with other known apparatus. Furthermore, the limited contact of the porous member with the piezoelectric substrate limits any loss of SAW energy through being absorbed by the porous member. This results in improved operational energy efficiency for the atomisation apparatus according to the present invention. In addition, the reduced temperature of the aerosols/droplets produced by the atomisation apparatus according to the present invention allows for the delivery of more temperature sensitive biological substances, chemicals or pharmaceuticals.

Modifications and variations as would be deemed obvious to the person skilled in the art are included within the ambit of the present invention as claimed in the appended claims.

The invention claimed is:

1. An apparatus for atomising liquid, including a piezoelectric substrate having a working surface, and a peripheral edge extending along a side of the working surface, an interdigital transducer located on the working surface for generating surface acoustic waves (SAW) in the working surface, and a liquid delivery arrangement including the liquid and a porous member for supplying the liquid to be atomised, wherein the porous member is in contact with the peripheral edge of the piezoelectric substrate and positioned relative to the peripheral edge such that an upper surface of the porous member is spaced a non-zero distance from the working surface equal to or less than a thickness of a boundary layer defined in a layer of the liquid formed over the working surface from the liquid drawn from the porous member by the SAW, the boundary layer being located immediately adjacent to the working surface.

2. The apparatus for atomising liquid according to claim 1, wherein the interdigital transducer is a DART-SPUDT.

3. The apparatus for atomising liquid according to claim 1, wherein the interdigital transducer has a thickness of at least 1% of the SAW wavelength.

4. The apparatus for atomising liquid according to claim 3, wherein the thickness of the interdigital transducer is between 1 to 5% of the SAW wavelength.

5. A method of pulmonary delivery of biological substances comprising: using the apparatus as claimed in claim 1 to deliver the biological substances.

6. The method of pulmonary delivery according to claim 5, wherein the biological substances include stem cells.

7. A method of delivery of pharmaceutical substances comprising: using the apparatus according to claim 1 to deliver the pharmaceutical substances.

8. A method of delivery of fragrant substances comprising: using the apparatus according to claim 1 to deliver the fragrant substances.

9. A method of delivering cosmetic substances comprising: using the apparatus according to claim 1 to deliver the cosmetic substances.

10. A method of generating sprays for a mouth and a throat of a person comprising: using the apparatus according to claim 1 to generate the sprays for the mouth and the throat of the person.

11. A method of generating sprays with cleaning, sterilizing and anti-allergy substances comprising: using the apparatus according to claim 1 to generate the sprays with the cleaning, sterilizing and anti-allergy substances.

12. A method of delivering agricultural chemicals including herbicides, fungicides, insecticides and fertilizers comprising: using the apparatus according to claim 1 to deliver the agricultural chemicals including the herbicides, fungicides, insecticides and fertilizers.

* * * * *

UNITED STATES PATENT AND TRADEMARK OFFICE
CERTIFICATE OF CORRECTION

PATENT NO. : 10,792,690 B2
APPLICATION NO. : 14/769490
DATED : October 6, 2020
INVENTOR(S) : James Friend et al.

It is certified that error appears in the above-identified patent and that said Letters Patent is hereby corrected as shown below:

On the Title Page

Item (71), Replace "RMIT UNIVERSITY, Melbourne (AU)" With --"ROYAL MELBOURNE INSTITUTE OF TECHNOLOGY, Melbourne (AU)"--

Signed and Sealed this
Eleventh Day of April, 2023

Katherine Kelly Vidal
Director of the United States Patent and Trademark Office